US010948328B2

United States Patent
Klomp

(10) Patent No.: US 10,948,328 B2
(45) Date of Patent: Mar. 16, 2021

(54) SYSTEM FOR MEASURING AN AMOUNT OF LIQUID IN AN ELASTIC BAG

(71) Applicant: FRITZ RUCK OPHTHALMOLOGISCHE SYSTEME GMBH, Eschweiler (DE)

(72) Inventor: Manfred Klomp, Hulsberg (NL)

(73) Assignee: FRITZ RUCK OPHTHALMOLOGISCHE SYSTEME GMBH, Eschweiler (DE)

( * ) Notice: Subject to any disclaimer, the term of this patent is extended or adjusted under 35 U.S.C. 154(b) by 152 days.

(21) Appl. No.: 16/330,864

(22) PCT Filed: Aug. 10, 2017

(86) PCT No.: PCT/EP2017/070291
§ 371 (c)(1),
(2) Date: Mar. 6, 2019

(87) PCT Pub. No.: WO2018/046221
PCT Pub. Date: Mar. 15, 2018

(65) Prior Publication Data
US 2019/0219434 A1 Jul. 18, 2019

(30) Foreign Application Priority Data

Sep. 6, 2016 (EP) .................................. 16187314

(51) Int. Cl.
*G01F 22/00* (2006.01)
*A61M 3/02* (2006.01)
(Continued)

(52) U.S. Cl.
CPC ........... *G01F 22/00* (2013.01); *A61M 1/0058* (2013.01); *A61M 3/022* (2014.02);
(Continued)

(58) Field of Classification Search
CPC ..... G01F 22/00; A61M 3/022; A61M 3/0216; A61M 3/0233; A61M 3/0254;
(Continued)

(56) References Cited

U.S. PATENT DOCUMENTS

| 5,563,584 A | 10/1996 | Rader et al. |
| 2014/0100518 A1* | 4/2014 | Baxter ...................... G01L 9/12 604/67 |

(Continued)

FOREIGN PATENT DOCUMENTS

DE 3637771 C1 12/1987

OTHER PUBLICATIONS

International Preliminary Report on Patentability of PCT/EP2017/070291 dated Mar. 21, 2019.
(Continued)

*Primary Examiner* — Suman K Nath
(74) *Attorney, Agent, or Firm* — Workman Nydegger

(57) ABSTRACT

A system for measuring an amount of liquid in an elastic bag, where there is formed in the lower area of the elastic bag a liquid opening for retrieving liquid from the elastic bag. The system includes push elements, which abut at opposite walls of the elastic bag and which are spaced apart from one another, a drive unit, which is configured to drive at least one push element, sensors, and a control unit. The sensors are configured to measure a liquid level of the liquid in the elastic bag. The control unit is configured to calculate an amount of liquid in the elastic bag on the basis of the liquid level and the distance between the push elements. The liquid level of the liquid in the elastic bag is changeable by reducing the distance between the push elements by means of the at least one drive unit.

9 Claims, 3 Drawing Sheets

Figure 1:
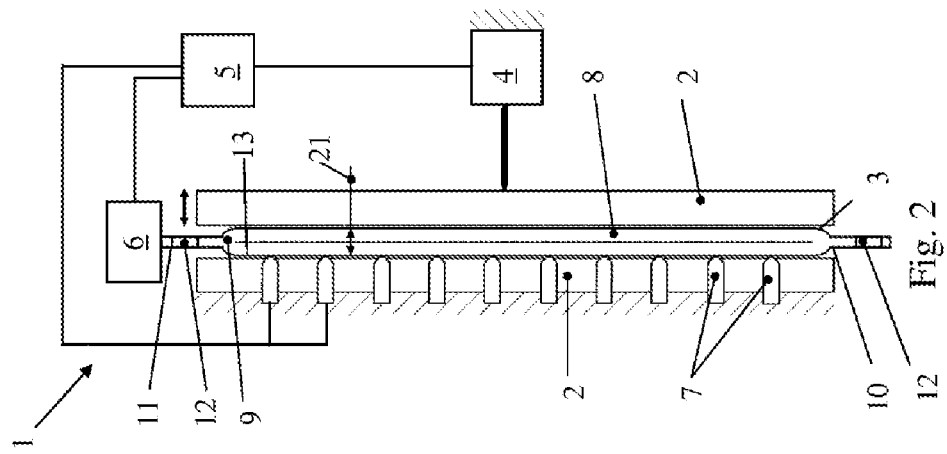

(51) Int. Cl.
   *A61M 1/00*      (2006.01)
   *A61M 5/152*     (2006.01)
   *A61M 5/168*     (2006.01)

(52) U.S. Cl.
   CPC ........ *A61M 3/0216* (2014.02); *A61M 3/0233* (2013.01); *A61M 5/152* (2013.01); *A61M 5/16804* (2013.01); *A61M 2205/3331* (2013.01); *A61M 2205/3379* (2013.01); *A61M 2210/0612* (2013.01)

(58) Field of Classification Search
   CPC ................ A61M 1/0058; A61M 5/152; A61M 5/16804; A61M 2210/0612; A61M 2205/3379; A61M 2205/3331; A61M 2205/0216
   See application file for complete search history.

(56) References Cited

U.S. PATENT DOCUMENTS

2014/0114236 A1* 4/2014 Gordon ............... A61F 9/00745
                                                      604/28
2014/0276639 A1   9/2014 Tarkeshian et al.

OTHER PUBLICATIONS

International Search Report dated Oct. 16, 2017 from International Patent Application No. PCT/EP2017/070291, filed Aug. 10, 2017.

\* cited by examiner

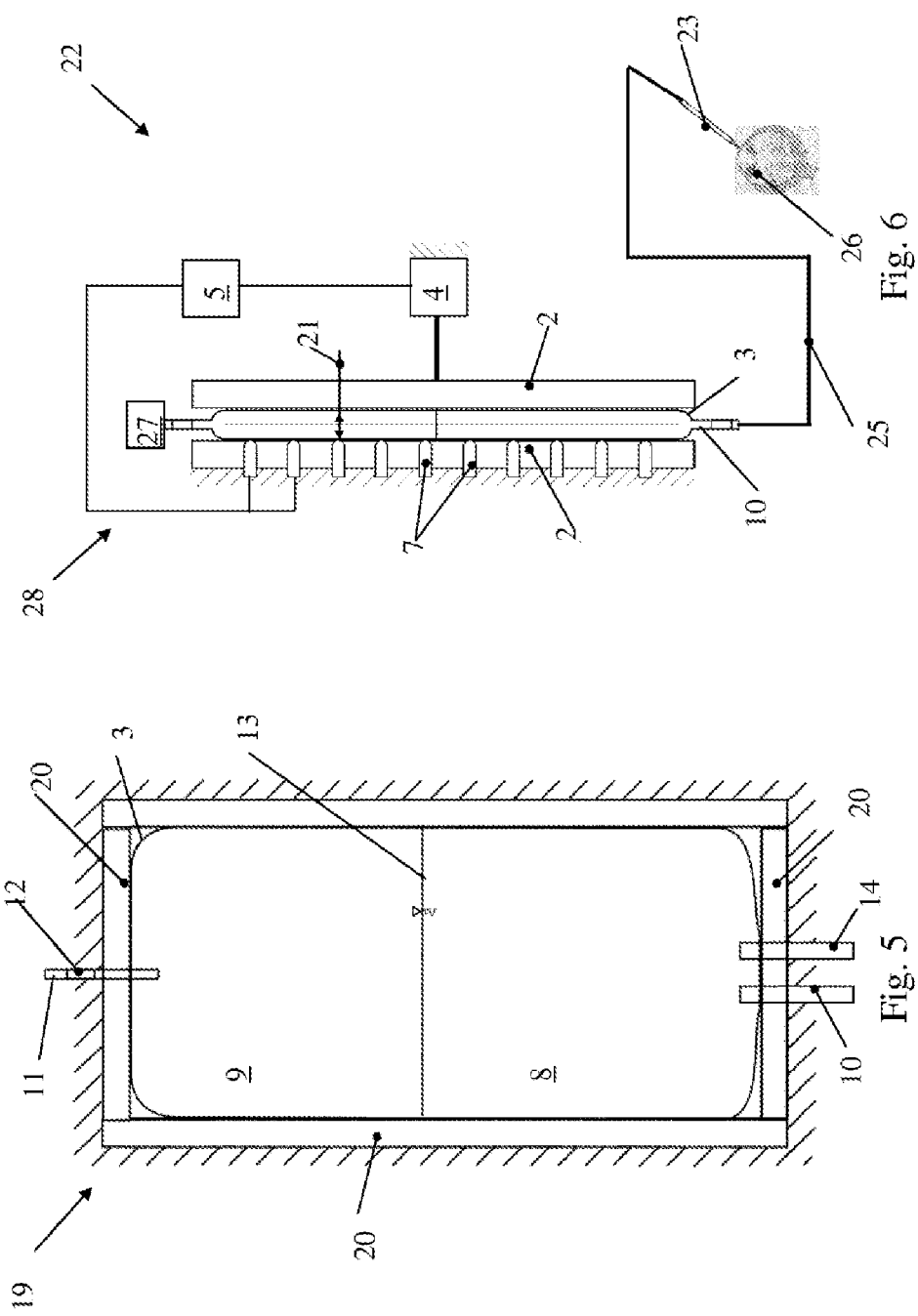

SYSTEM FOR MEASURING AN AMOUNT OF LIQUID IN AN ELASTIC BAG

The present application is a U.S. National Stage of International Application No. PCT/EP2017/070291, filed on Aug. 10, 2017, designating the United States and claiming the priority of European Patent Application No. 16187314.6 filed with the European Patent Office on Sep. 6, 2016. All of the aforementioned applications are incorporated herein in their respective entireties by this reference.

The invention relates to a system for measuring an amount of liquid in an elastic bag, wherein the elastic bag has a gas phase in addition to the liquid phase formed by the liquid and wherein in the operational position of the elastic bag there is formed in the lower area of the elastic bag a liquid opening for retrieving liquid from the elastic bag, having at least two push elements, which abut at opposite walls of the elastic bag and which are spaced apart from one another, at least one drive unit, which is configured to drive at least one push element, wherein the at least two push elements may be moved towards one another by driving at least one push element, at least one sensor, and a control unit, which is configured to communicate with the at least one sensor and the at least one drive unit.

The publication U.S. Pat. No. 6,491,661 B1 discloses a pressure regulation system for an infusion device, which includes an elastic bag, two push elements in the form of plates, two springs, one valve, one pressure sensor and two drive units. The elastic bag is connected to the valve via attachment to a liquid opening of the elastic bag via a flexible hose. One of the plates is movably mounted, and the other plate is fixed using additional elements not explained in greater detail, wherein the two drive units are configured to drive the movably mounted plate. The plates are arranged in parallel to another and abut at opposite walls of the elastic bag, whereby the elastic bag is clamped between the plates. By reducing a distance between the plates by driving the movably mounted plate by means of two drive units, a pressure in the bag and, consequently, a liquid pressure, at which liquid is discharged from the elastic bag, may be increased, wherein by means of the pressure sensor and an integrated controller, a predetermined pressure may be maintained in the elastic bag. The pressure regulation system further has a volume flow sensor, which measures a discharge rate of liquid from the elastic bag, whereby an amount of the liquid already discharged from the elastic bag may be calculated.

A similar pressure regulation system is also known from the publication US 2014/0114236 A1.

With the pressure regulation system known from the publication U.S. Pat. No. 6,491,661 B and the publication US 2014/0114236 A1 there has been proven to be disadvantageous that the liquid has to flow through the volume flow sensor in order to measure the discharge rate of liquid from the elastic bag. Consequently, this has to be cleaned or replaced after a change of the type of liquid and following every single use in order to prevent the contamination of the liquid by residues in the volume flow sensor.

In order to overcome this disadvantage, there have been made first efforts to attach sensors externally to the bags, which are configured to measure a liquid level within the elastic bag, whereby, when the volume of the elastic bag is known, the amount of liquid in the elastic bag may be calculated on the basis thereof. Accuracy of the indication of the liquid level, thus, is dependent on the number of sensors, which are applied to the bag. In the case of a high number of sensors, however, it is highly probable that a failure of individual sensors will not be immediately detected, whereby the liquid level in the elastic bag cannot be correctly determined anymore. Such a system is further expensive due to the high number of sensors.

It is the task of the present invention to provide a system for measuring an amount of liquid in an elastic bag, which overcomes the disadvantages of prior art and for which an amount of liquid in the elastic bag may be determined by means of a small number of sensors without direct contact with the liquid.

According to the invention this task is solved by the elastic bag having a gas opening, which extends into the gas phase, and by the at least one sensor being configured to measure a liquid level of the liquid in the elastic bag, wherein the control unit is configured to calculate an amount of liquid in the elastic bag on the basis of the liquid level and the distance between the at least two push elements and wherein the liquid level of the liquid in the elastic bag may be changed by reducing the distance between the at least two push elements by means of the at least one drive unit.

In this way, there is obtained the advantage that only a small number of sensors, more particularly at least one sensor, is necessary in order to determine the liquid level in the elastic bag with sufficient accuracy. The at least one sensor is advantageously applied at a particular height of the elastic bag either in a push element or directly onto the wall of the elastic bag. If the at least one sensor is, for example, attached at half the height of the wall of the elastic bag, it will signalize when the liquid level has dropped to the half and the elastic bag is half empty. By means of the control unit, then the distance between the at least two elements will be reduced, whereby the elastic bag is compressed and whereby the liquid level in the elastic bag will then be lifted again, even though a smaller amount of liquid is in the elastic bag. Consequently, due to the inventive embodiment of the system, the measurement of the amount of liquid will become more accurate, the more the distance between the at least two push elements is being reduced.

The at least one sensor is usefully formed by a capacity sensor or an optical sensor. If at least one capacitive sensor is used, then the sensor elements thereof will be advantageously applied to the opposite walls of the elastic bag. In a further embodiment the sensor elements may also be arranged respectively in the push elements.

If several sensors are present, then the sensor are advantageously arranged on at least one push element in equal intervals to one another along an in the operational position essentially vertical axis. If there are used several sensors, the accuracy of the system may be further increased, wherein the system will function always more accurately with an equal number of sensors than systems known form prior art.

The elastic bag preferably has an essentially plane shape. Especially preferably the elastic bag is formed from a plastic film, which is folded over and which is sealed at the edges thereof. In this way there is obtained the advantage that the push elements, which advantageously also have a planar shape and are preferably formed by plates, abut in a plane way at the walls of the elastic bag. An area of the plates, via which the plates abut at the walls of the elastic bag, is usefully the same as or larger than areas of the walls. The plates are arranged preferably in parallel to one another and in parallel to the elastic bag. In this way there is obtained the advantage that, if the plates move towards one another, then the entire elastic bag will be compressed and bulges of the elastic bag may be greatly prevented. There is further given the advantage that the elastic bag may be emptied completely, apart from some smaller residues, thus preventing unnecessary waste of liquid.

The gas opening is preferably formed by first tube, which in the operational position of the elastic bag projects from an upper side of the elastic bag into the gas phase or which in the operational position of the elastic bag projects from a lower side of the elastic bag into the gas phase. The liquid opening is advantageously formed by a second tube. By the gas opening and the liquid opening being formed as tubes, these may be very easily, in the case of an elastic bag formed from a plastic film that is folded over and sealed at the edges, put between the folded-over plastic film and sealed therewith during production. If the first tube projects from a lower side of the elastic bag into the gas phase, there is given the advantage that the gas opening and the liquid opening are arranged on one side, namely in the operational position of elastic bag, at the lower side of the elastic bag, whereby handling of the elastic bag will be facilitated.

The system usefully has a ventilation unit, which is connected to the control unit for communication and which connects to the gas opening of the elastic bag. In this way there is obtained the advantage that a liquid pressure within the elastic bag may be regulated by means of the ventilation unit, controlled by the control unit independently of the movement of the push elements.

Further advantageous embodiments of the system according to the invention will be explained in greater detail in the following by way of the figures.

Figure 2:
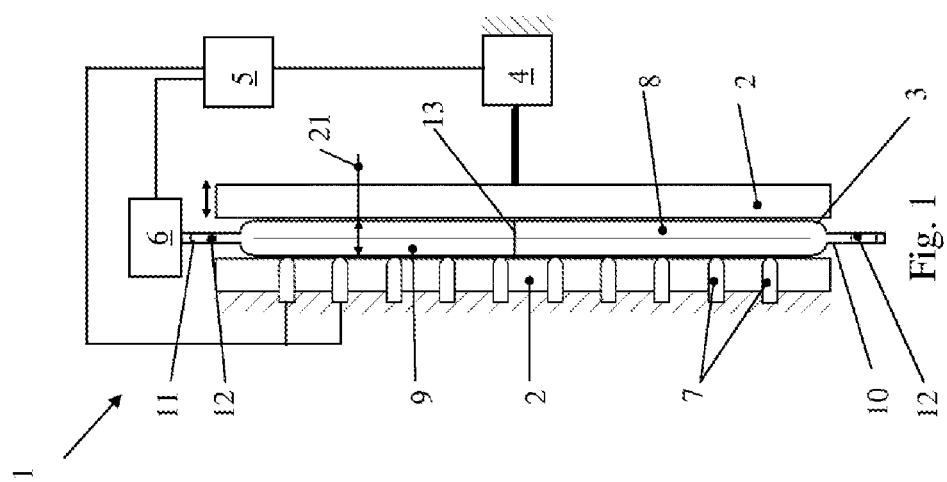

The FIGS. 1 and 2 show a first embodiment of the system according to the invention, respectively in a schematic side view.

Figure 3:
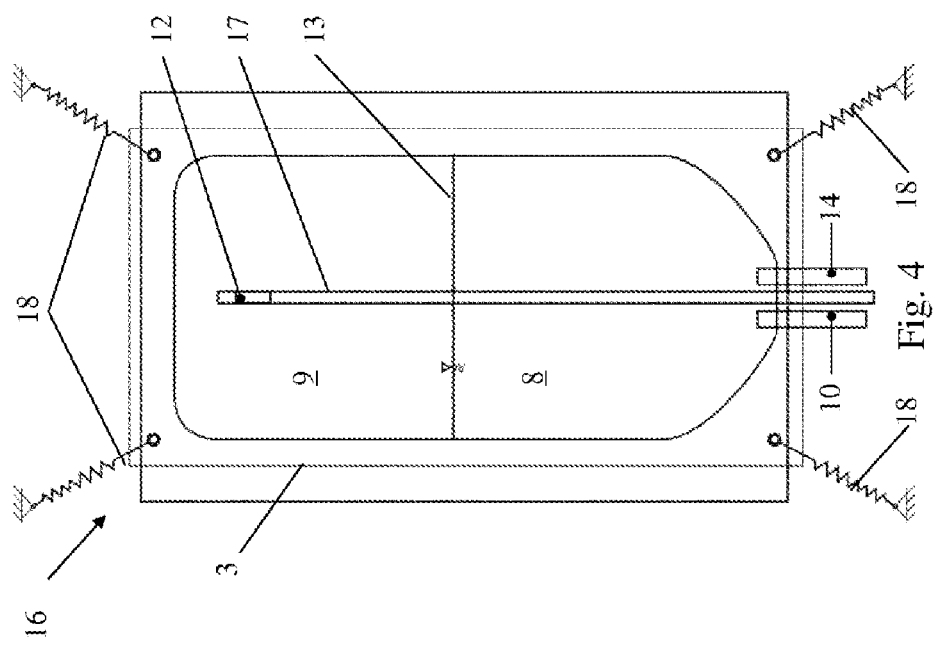

FIG. 3 shows the first embodiment of the system according to the invention according to FIG. 1 in a schematic side view.

Figure 4:
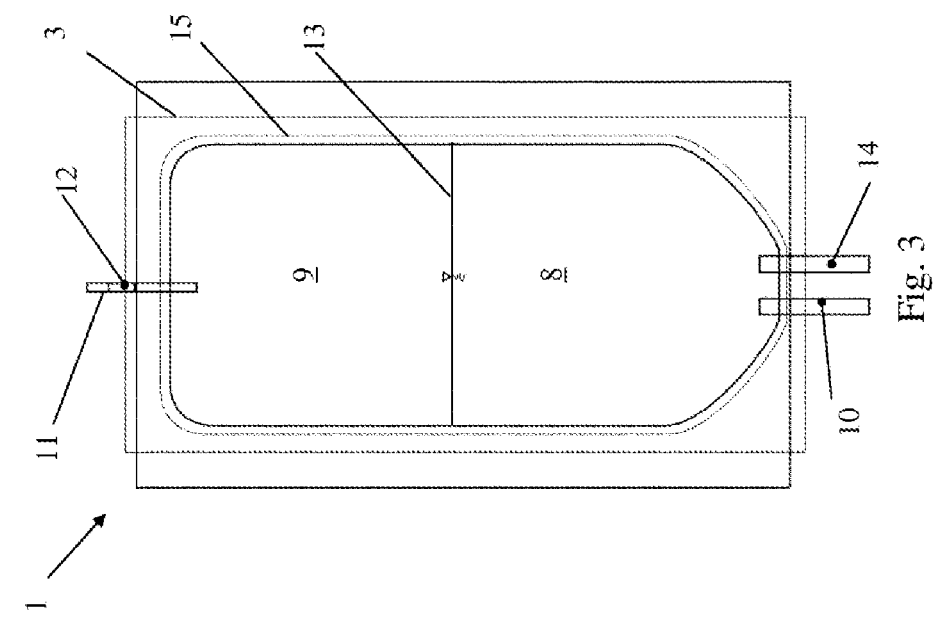

The FIGS. 4 and 5 each show a further embodiment of the system according to the invention in a schematic side view.

FIG. 6 shows a further embodiment of the system according to the invention when used in an ophthalmic surgery device in a schematic illustration.

The FIGS. 1 and 2 show a first embodiment of the system 1 according to the invention respectively in a schematic side view. The system 1 comprises two push elements formed by plates 2, an elastic bag 3, a drive unit 4, a control unit 5, a ventilation unit 6 and ten sensors 7. The elastic bag 3 has a liquid phase 8 and a gas phase 9, and in its operation position it is oriented vertically. A liquid of the liquid phase 8 may, for example, be formed by infusion liquid, in particular saline, or irrigation liquid. A gas of the gas phase 9 is advantageously formed by air. The elastic bag 3 has in the lower area an injection opening and a liquid opening, which liquid opening is formed by a second tube 10 and through which liquid may be discharged from the liquid phase 8 of the elastic bag 3. The injection opening is illustrated in FIG. 3 and serves for injecting liquid or additives, which are to be added to the liquid in the elastic bag 3, for example before the beginning of a surgical intervention. The injection opening is formed by a third tube 14. In the upper area of the elastic bag 3 there is formed a gas opening, which gas opening is formed by a first tube 11. The first tube 11 extends into the gas phase 9 of the elastic bag 3 and is connected to the ventilation unit 6. The plates are arranged in parallel and in a distance to one another, respectively abutting at the opposite walls of the elastic bag 3. Consequently, the elastic bag 3 is arranged clamped between the plates 2. One plate 2 is fixed, and the other plate 2 is movably mounted, wherein the movably mounted plate 2 may be driven by the drive unit 4 such that the plates 2 may be moved towards one another, whereby a distance 21 between the plates 2 may be reduced. The drive unit 4 is advantageously formed by a rack and pinion drive that is driven by an electric motor, a threaded bar drive that is driven by an electric motor, a pneumatically driven cylinder or a hydraulically driven cylinder.

The sensors 7 as well as the ventilation unit 6 and the drive unit 4 are connected to the control unit 5 for communication. For clarity reasons, not all ten sensors 7 are connected to the control unit 5 in the FIGS. 1 and 2. The sensors 7 are formed by optical sensors, wherein these will emit a sensor signal, indicating the detection of liquid, if the probe tips thereof abut at the bag 3 in the area of the liquid phase 8. Such optical sensors are known to those skilled in the art. The sensors 7 are arranged on a plate 2 in equal intervals to one another along an in the operational position of the system 1 vertical axis. Consequently, a liquid level 13 in the elastic bag 3 may be detected by the control unit 5 using the sensors 7.

The ventilation unit 6 comprises a proportional pressure valve and a compressor unit for compressing ambient air.

In the first tube 11 as well as in the second tube 10 and the third tube 14, there are respectively formed anti-break means 12, wherein the tubes 10, 11 and 14 will only be approved for use in a surgical intervention if the anti-break means 12 have been buckled.

In the following there is described in greater detail the functional mode of the system 1 according to the invention, wherein an elastic bag 3 that is fully filled with the liquid is assumed. For this purpose, there was arranged a newly filled elastic bag 3 between the plates 2, or an elastic bag 3 that has already been arranged between the plates 2 is refilled with the liquid by means of an auxiliary device via the third tube 14.

By means of the proportional pressure valve of the ventilation unit 6, a pressure in the elastic bag 3 is regulated by a gas supply into the elastic bag 3 and/or a gas discharge from the elastic bag 3 that is controlled by the control unit 5. The pressure in the elastic bag 3 is thereby advantageously adjusted directly at the control unit 5. The liquid pressure in the second tube 10, due to the weight of the liquid, is slightly higher than the pressure adjusted by the proportional pressure valve in the elastic bag 3, wherein a pressure that is lower than an ambient pressure may be applied onto the elastic bag 3 temporarily by the ventilation unit 6 in order to prevent undesired leakage from the second tube 10. By providing an additional valve, connected to the second tube 10, this function may be omitted. With the system 1, the discharge of liquid is only controlled by the ventilation unit 6, wherein already a slightly higher pressure than the ambient pressure or a pressure equal to the ambient pressure, depending on the amount of liquid in the elastic bag 3, will be sufficient in order to discharge liquid form the elastic bag 3. The sensor 7 continuously detect the liquid level 13 during the discharge of liquid from the second tube 10, wherein, if it dips below a predetermined liquid level 13, the control unit 5 controls the drive unit 4 to move the plates 2 towards one another in order to reduce the distance 21 between the plates 2. By moving the plates 2 towards one another, a volume of the elastic bag 3 is reduced, and as a consequence a volume of the gas phase 9 is reduced.

With the system 1 according to the invention depicted in FIG. 1, the liquid level 13 has dropped to the half thereof, and the elastic bag 3 is only half filled. With the system 1 according to the invention depicted in FIG. 2, the distance 21 between the plates 2 in respect to the distance 21 according to FIG. 1 has been reduced by half, whereby the liquid level 13 has again risen to the top of the elastic bag 3. If the liquid level 13 then again drops to the half thereof, the elastic bag 3 will still be filled with a quarter of the original amount of liquid. This process is continued until the elastic bag 3 is empty or until the elastic bag 3 has been emptied to a predetermined amount.

The control unit 5, by knowing the distance 21 between the plates 2 and position of the liquid level 13 measured by the sensors 7, is configured to detect the amount of liquid present in the elastic bag 3, wherein measurement accuracy of the amount of liquid present will increase with the distance 21 being reduced. Moving the plates 2 towards one another and the reduction of the distance 21 between the plates 2 as a result thereof results not only in a reduction of the volume of the gas phase 9, whereby inertia of the system 1 in the case of pressure changes will be prevented, but rather in an increase of the measurement accuracy of the amount of liquid, which is still present in the elastic bag 3, with the constant number of sensors 7.

In a further embodiment the sensors 7 are formed by capacitive sensors, wherein respectively one capacitive sensor has two sensor elements, which are each attached opposite to another at the plates 2.

FIG. 3 shows the first embodiment of the system 1 according to the invention according to FIG. 1 in a schematic sectional view. The elastic bag 3 consists of an one-piece plastic film which is folded over and sealed at the edges 15 of the plastic film.

FIG. 4 shows a further embodiment of the system 16 according to the invention in a schematic front view. The system 16 differs from the system 1 shown in the FIGS. 1 to 3 in that it has extension elements in the form of springs 18. The elastic bag 3 is extended by the springs 18 transversely to the movement of the movably mounted plates 2 when the plates 2 are moved towards one another, whereby the elastic bag 3 is prevented from collapsing or folding, respectively, thus retaining essentially the form thereof.

In the system 16 a first tube 17 forming the gas opening further extends from the lower side of the elastic bag 3 into the gas phase 9. In this way there is obtained the advantage that all connections are arranged on one side of the elastic bag 3.

FIG. 5 shows a further embodiment of the system 19 according to the invention in a schematic front view. The system 19 differs from the system shown in FIG. 1 in that the system 19 has side walls 20. The side walls 20 are each fixed at auxiliary elements, in particular a frame, and they are formed by further plates, wherein the driven plate 2 may move in relation to the further plates. This gives the advantage that lateral deflection of the elastic bag 3 or bulging of the elastic bag 3 will be prevented also in the case of high pressures, wherein the liquid pressure may also be well-regulated in the case of high pressure, not resulting in inertia of the system 19 due to the expansion of the elastic bag 3.

FIG. 6 shows a further embodiment of the system 28 according to the invention when used in an ophthalmic surgical device 22 in a schematic illustration. The system 28 differs from the system 1 shown in the FIGS. 1 to 3 in that in the system 28 the ventilation unit is formed by a simple filter 27.

The ophthalmic surgical device 22 additionally to the system 28 comprises a surgical tool holder 23, wherein the surgical tool holder 23 is connected by way of a hose 25 directly to the second tube 10 and has a control valve not depicted. The control valve may, for example, be formed by a magnetic valve, wherein an amount of liquid that is discharged into an eye 26 is regulated by the control valve. During the discharge of liquid into the eye 26 ambient air will flow into the elastic bag 3 via the filter 27, and if the distance 21 is reduced, air will be discharged from the elastic bag 3 via the filter 21 into the surroundings. An irrigation pressure required for a surgical intervention is obtained by a difference in height between the elastic bag 3 and the surgical tool holder 23. The amount of liquid in the elastic bag 3 is continuously detected via the sensors 7 and the distance 21 between the plates 2 by means of the control unit 5, and if it dips below a determined amount of liquid in the elastic bag 3, the control unit 5 will emit a warning signal.

In a further embodiment the ventilation unit 6 is formed by a valve that may be controlled by the control unit 5.

It is to be noted that a device according to the invention for measuring the amount of liquid may be used as a filling level indicator in a plurality of devices of most diverse technical fields. Such a filling level indicator could, for example, be used for measuring the filling level of the windshield washer fluid in a car or for measuring the filling level of a soft drink in a soda machine. In the case of a milking machine, the amount of milk already milked could be measured, and in the case of a urinary bag, the amount of urinary already excreted by a patient could be measured.

The control unit could also process sensor signals of sensors that are arranged in different intervals to one another, wherein the resolution of measuring could be further increased for a particular liquid level by sensors that are positioned closer to one another. There could, for example, be arranged a plurality of sensors only at a medium height of the bag, close to one another, wherein the position of the push elements will ensure that the liquid level will always be maintained within the measurement area of these sensors. In this way there is obtained the advantage that a very high resolution of measurement may be achieved using fewer sensors.

The invention claimed is:

1. A system for measuring an amount of liquid in an elastic bag, wherein the elastic bag comprises:
   a gas phase in addition to the liquid phase formed by the liquid, wherein in the operational position of the elastic bag there is formed in the lower area of the elastic bag a liquid opening for retrieving liquid from the elastic bag;
   the system further comprising: at least two push elements, the at least two push elements abut at opposite walls of the elastic bag and the at least two push elements are spaced apart from one another;
   at least one drive unit, wherein the at least one drive unit is configured to drive at least one of the at least two push elements, wherein the at least two push elements may be moved towards one another by driving the at least one push element of the at least two push elements;
   at least one sensor;
   a control unit, wherein the control unit is configured to communicate with the at least one sensor and the at least one drive unit; and
   a gas opening, wherein the gas opening opens into the gas phase;
   wherein the at least one sensor is configured to measure a liquid level of the liquid in the elastic bag, wherein the control unit is configured to calculate an amount of liquid in the elastic bag on the basis of the liquid level and the distance between the at least two push elements, and wherein the liquid level of the liquid in the elastic bag is changeable by reducing the distance between the at least two push elements by the at least one drive unit.

2. The system according to claim 1, wherein the at least one sensor is a capacitive sensor or an optical sensor.

3. The system according to claim 1, wherein the at least one sensor comprises a plurality of sensors, and the sensors of the plurality of sensors are arranged on at least one push element of the at least two push elements or are applied onto the elastic bag in equal intervals to one another along an operational position of the system essentially vertical axis.

4. The system according to claim 1, wherein the elastic bag has an essentially plane shape.

5. The system according to claim 1, wherein the elastic bag is formed from a plastic film that is folded over, which is sealed at the edges thereof.

6. The system according to claim 1, wherein the gas opening is formed by a first tube, which in the operational position of the elastic bag projects from an upper side of the elastic bag into the gas phase or which in the operational position of the elastic bag projects from a lower side of the elastic bag into the gas phase.

7. The system according to claim 1, wherein the at least two push elements are formed by plates, which are arranged in parallel to one another.

8. The system according to claim 1, wherein the system has a ventilation unit, which is connected to the control unit for communication and which connects to the gas opening of the elastic bag.

9. A method for measuring an amount of liquid in an elastic bag, which has a gas phase, having a system according to claim 1, wherein when the liquid level dips below a determined liquid level in the elastic bag, the at least one drive unit is controlled to reduce the distance between the at least two push elements.

* * * * *